United States Patent [19]
Adamkowski et al.

[11] Patent Number: 5,706,327
[45] Date of Patent: Jan. 6, 1998

[54] METHOD AND APPARATUS FOR MAMMOGRAPHIC COMPRESSION

[75] Inventors: Mike Adamkowski, Union, N.J.; Richard R. Bird, Bethel; Debra S. Saunders, Danbury, both of Conn.

[73] Assignee: Trex Medical Corporation, Danbury, Conn.

[21] Appl. No.: 599,597

[22] Filed: Feb. 9, 1996

[51] Int. Cl.[6] .................................................. A61B 6/04
[52] U.S. Cl. ................................... 378/37; 378/208
[58] Field of Search ....................... 378/37, 195, 208; 128/653.1, 660.01, 660.09, 660.1, 661.01, 915

[56] References Cited

U.S. PATENT DOCUMENTS

| | | |
|---|---|---|
| 3,556,081 | 1/1971 | Jones . |
| 3,971,950 | 7/1976 | Evans et al. . |
| 4,658,409 | 4/1987 | Summ . |
| 4,962,515 | 10/1990 | Kopans . |
| 5,029,193 | 7/1991 | Saffer . |
| 5,040,198 | 8/1991 | Hixson, Sr. . |
| 5,050,197 | 9/1991 | Virta et al. ........................ 378/37 |
| 5,289,520 | 2/1994 | Pellegrino et al. .................. 378/208 |
| 5,305,365 | 4/1994 | Coe . |
| 5,506,877 | 4/1996 | Niklason et al. .................... 378/38 |

OTHER PUBLICATIONS

"New Contoured-Tilting Compression System for Mammography Imaging", Jameson-Meehan, et al. no date.

*Primary Examiner*—Don Wong
*Attorney, Agent, or Firm*—Ware, Fressola, Van Der Sluys & Adolphson LLP

[57] ABSTRACT

A compression apparatus for use with conventional mammography apparatus is disclosed. The apparatus comprises a frame which may be attached to a conventional mammography device's compression paddle carriage. The apparatus further comprises a compression surface having a chest wall end and a nipple end, pivotally attached to the frame at a pivot point located between the chest wall end and the nipple end. To provide adequate compressive forces at the chest wall end of the compression surface while allowing rotation about the pivot point, a spring is attached between the frame and the compression surface at the nipple end of the compression surface.

12 Claims, 3 Drawing Sheets

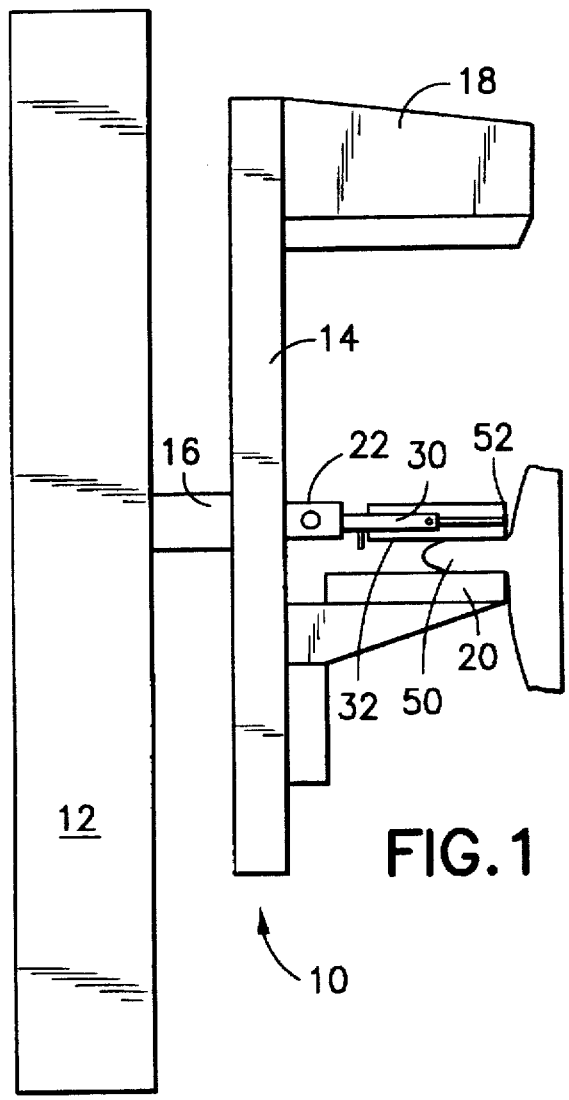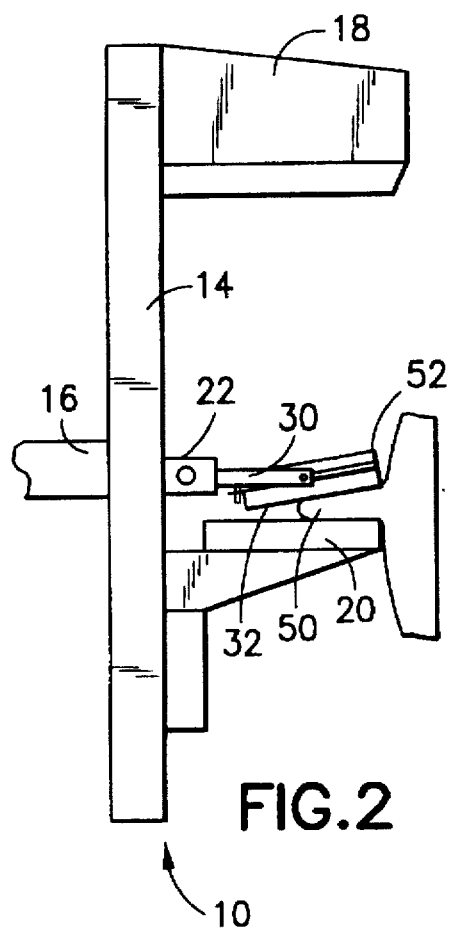

5,706,327

METHOD AND APPARATUS FOR MAMMOGRAPHIC COMPRESSION

BACKGROUND OF THE INVENTION

1. Field of the Invention

The present invention generally relates to medical X-ray imaging and particularly to mammography. More specifically, the present invention relates to a method and apparatus for mammographic compression which enables compressive forces to be distributed more uniformly along the breast while still providing sufficient compression at the chest wall.

2. Description of the Prior Art

In mammography, a breast is compressed between a compression paddle or surface and a breast support platform, which may be the image receiver in some cases. The compressed breast is exposed to X-rays to obtain a mammographic image or mammogram. It is well known that in mammography the breast is compressed for several reasons, including: to obtain higher contrast images with better X-ray penetration and lower X-ray energy; to spread the breast tissue out so that there are less superimposed structures in a mammographic image; and to reduce scattered radiation, which also helps to improve image contrast and, in turn, image quality. Thus, sufficient compression of the breast is one of several important factors required to obtain high quality mammographic images.

In prior art breast compression apparatus, the compression surface is rigidly fixed to a frame and positioned so as to be co-planar to a breast support platform surface. With such prior art compression apparatus used with conventional mammography devices, breast compression can be non-uniform along the breast, with the greatest compression closest to the chest wall and the least compression towards the nipple where the breast is relatively thinner.

One of the other known drawbacks with the rigidly fixed prior art compression paddles is movement of the breast tissue near the nipple end of the breast during imaging, which can cause image blurring, because the nipple end is not compressed sufficiently. Also, in some cases with the prior art rigidly fixed compression surfaces, mammography patients could experience an undesirable pinching feeling near the chest wall where the compression surface applies the greatest compression.

SUMMARY OF THE INVENTION

Accordingly, it is one object of the present invention to provide a simple, inexpensive compression paddle apparatus for a mammography device that provides greater compression at the nipple end of the breast while still providing sufficient compression at the chest wall end of the breast.

This object is accomplished, at least in part, by providing a rotatable compression paddle apparatus for a mammography device. The apparatus comprises a frame which may be attached to a conventional mammography device's compression paddle carriage. The apparatus further comprises a compression surface having a chest wall end and a nipple end, pivotally attached to the frame at a pivot point located between the chest wall end and the nipple end. To provide adequate compressive forces at the chest wall end of the compression surface while allowing rotation about the pivot point, a rotation resistance providing means is attached between the frame and the compression surface at its nipple end.

Other objects and advantages of the present invention will become apparent to those skilled in the art from the following detailed description read in conjunction with the attached drawings and claims appended hereto.

BRIEF DESCRIPTION OF THE DRAWINGS

The drawings, not drawn to scale, include:

FIG. 1 is a schematic side view of a conventional mammography device employing the compression paddle apparatus of the present invention illustrating the position of the planar compression surface at pre-contact and upon initial compression contact with a breast;

FIG. 2 is a schematic side view of the conventional mammography device employing the compression apparatus of the present invention illustrating the position of the planar compression surface upon final compression contact with a breast;

BEST MODE FOR CARRYING OUT THE INVENTION

Figure 3:
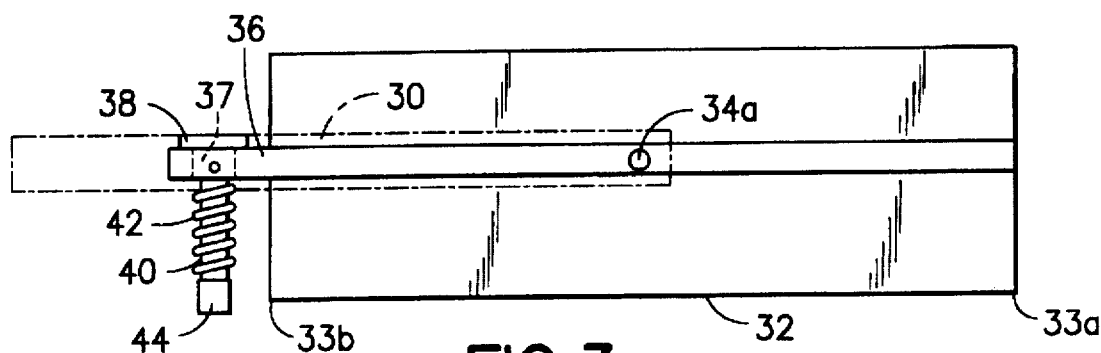
FIG. 3 is a schematic side view of the preferred embodiment of the compression paddle apparatus of the present invention corresponding to its precontact and initial contact positions in FIG. 1, illustrating a means for providing resistance to the rotation of the planar compression surface.

FIG. 1 illustrates a conventional mammography device 10 upon which the present invention may be used. The mammography device 10 comprises a base 12, an imaging C-arm 14 which is connected to the vertical travel assembly 12 via a pivot member 16, a X-ray tube 18 located at one end of the imaging C-arm 14 and an image receiver 20, which also provides a breast supporting surface, at the opposite end. A compression paddle stage 22 is slidably attached to the imaging arm 14 between the X-ray tube 18 and the image receiver 20.

Figure 4:
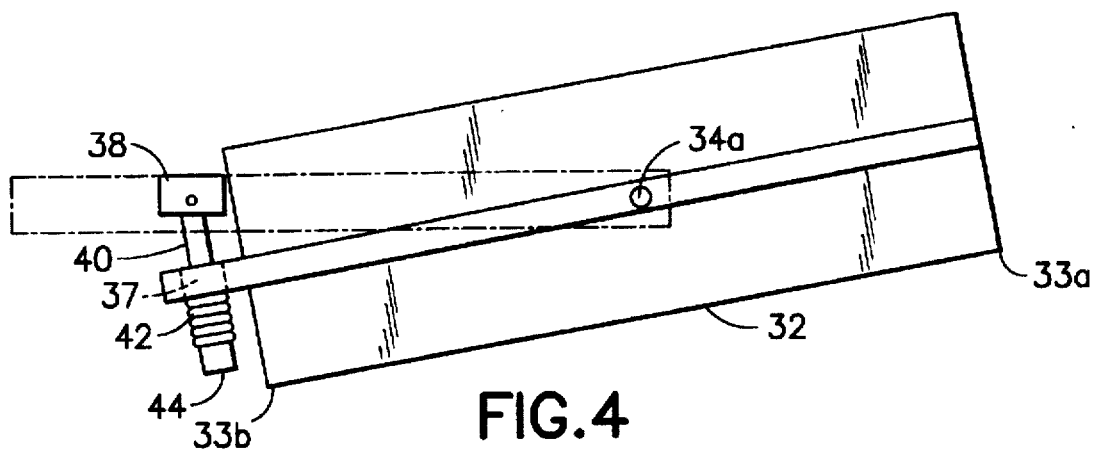
FIG. 4 is a schematic side view of the preferred embodiment of the compression paddle apparatus of the present invention corresponding to its position in FIG. 2, illustrating rotation of the planar compression surface against spring-lever resistance.
Figure 5:
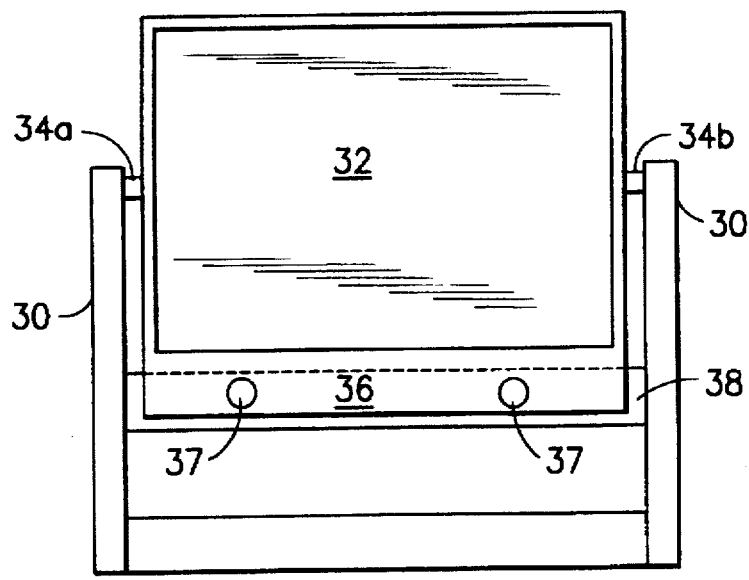
FIG. 5 is a schematic bottom view of the compression paddle apparatus of the present invention.

Referring to FIGS. 3 through 5, the preferred embodiment of the compression paddle apparatus of the present invention includes a frame 30 which may be attached to the slidable compression paddle stage 22. The apparatus further includes a compression surface 32, which is shown as substantially planar, having a chest wall end 33a and nipple end 33b. The compression surface 32 is attached to the frame 30 at pivots 34a and 34b located between chest wall end 33a and nipple end 33b. A lever member 36 is attached to the compression surface 32 and extends outwardly beyond the nipple end 33b towards the imaging arm 14. The lever member 36 includes opening 37.

A cross member 38 spans frame 30 adjacent to the nipple end 33b of the compression surface 32. At least one adjustable spring retaining member 40 is attached to cross member 38 and positioned through opening 37 of lever 36. A spring 42, such as a metal coil spring or an elastomer spring, is positioned between lever 36 and spring retaining end 44 of spring retaining member 40. As those skilled in the art will appreciate, a screw may be used as a spring retaining member 40, and through turning the screw into cross member 38, fine tuning of spring compression can be achieved. A bolt and nut combination may also be used as a spring retaining member 40 and would also allow fine tuning of spring compression.

As illustrated by FIGS. 1 through 4, in operation, the compression surface 32 of the present invention is angularly displaced or rotated about pivots 34a and 34b from a pre-contact resting position (FIG. 3) to a post-contact rotated position (FIG. 4) once the chest wall end 33a of the compression surface 32 makes contact with a patient's breast 50 at chest wall 52. By rotation of the compression surface 32 such that it is no longer co-planar with the surface created by the image receiver 20 (FIG. 2), better compression of the breast between the chest wall and nipple can be obtained. In order to ensure adequate compression at the chest wall 52, the rotation of the compression surface 32 about pivots 34a and 34b is met with resistance provided by compression of spring 42 between lever 36 and end 42 of spring retaining member 40 (illustrated in FIG. 4). A compressive force of approximately 25 pounds at chest wall end 33a with rotation of compression surface 32 can be obtained by using a suitable size spring, for example, one which will provide 25 pounds of resistance between lever 36 and end 42, assuming that the pivots 34a and 34b are at the midpoint between the nipple end 33b and the chest wall end 33a of the compression surface 32. Of course, if the pivots 34a and 34b are not at the midpoint, a different size spring will be necessary depending the position of pivots 34a and 34b.

Figure 6:
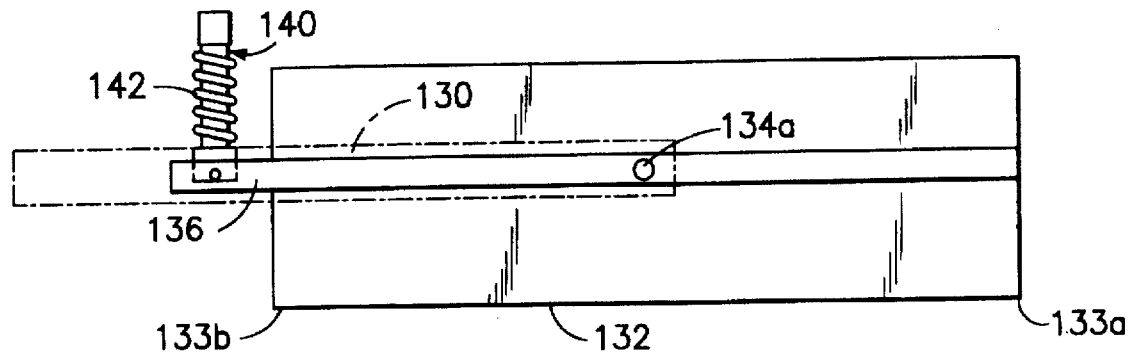
FIG. 6 is a schematic side view of an alternative embodiment of the compression paddle apparatus of the present invention corresponding to its pre-contact and initial contact positions as illustrated in FIG. 1, illustrating a means for providing resistance to the rotation displacement of the planar compression surface.
Figure 7:
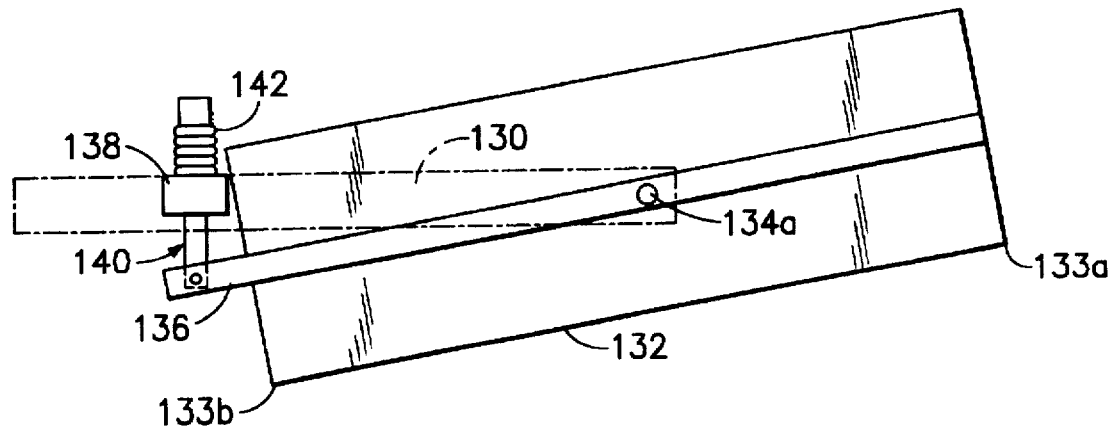
FIG. 7 is a schematic side view of the alternative embodiment of the compression paddle apparatus of the present invention corresponding to its position in FIG. 2, illustrating rotation of the planar compression surface against spring-lever resistance.

Referring to the alternative embodiment illustrated in FIGS. 6 and 7, similar to the preferred embodiment, a frame 130 is attached to the slidable compression paddle stage 22. A compression surface 132 having a chest wall end 133a and a nipple end 133b. The surface 132 is attached to the frame 130 at pivots 134a located between chest wall end 133a and nipple end 133b. A lever member 136 is attached to the compression surface 132 and extends outwardly beyond the nipple end 133b towards the imaging arm (not shown) of the mammography apparatus (not shown).

A cross member 138 having an opening therein 137 spans frame 130 adjacent to the nipple end 133b of the compression surface 132. Adjustable spring retaining member 140 is attached, preferably in a hinged manner, to lever 136 and positioned through openings 137 of cross member 138. A spring 142, metal coil or elastomeric, is positioned between cross member 138 and spring retaining end 144 of spring retaining member 140.

As illustrated by comparing FIGS. 6 and 7, in operation, the compression surface 132 of the present invention is rotated about pivot 134a from a pre-contact resting position (FIG. 6) to a post-contact rotated position (FIG. 7) when chest wall end 133a of the compression surface 132 makes contact with a patient's breast at the chest wall. By rotation of the compression surface 132 such that it is no longer co-planar with the surface created by the image receiver 20 (FIG. 2), better compression of the breast between the chest wall and nipple can be obtained. In order to ensure adequate compression at the chest wall, the rotation of the compression surface 132 about pivot 134 is met with resistance provided by compression of spring 142 between cross member 138 and end 142 of spring retaining member 140 (illustrated in FIG. 7).

It will thus be seen that the objects and advantages set forth above and those made apparent from the preceding descriptions, are efficiently attained and, since certain changes may be made in the above construction without departing from the scope of the invention, it is intended that the matter contained in the above description or shown in the accompanying drawings shall be interpreted as illustrative and not in a limiting sense. It is also to be understood that the following claims are intended to cover all of the generic and specific features of the invention herein described, and all statements of the scope of the invention which, as a matter of language, might be said to fall therebetween.

What is claimed is:

1. A method for compressing breast tissue for mammography, the method comprising the steps of:

providing a mammography device comprising:
an imaging arm having an X-ray source end and an image receiving end,
an X-ray source attached to the imaging arm at the imaging end,
a breast supporting X-ray image receiver attached to the imaging arm at the image receiving end;

providing a rotatable compression paddle apparatus for a mammography device between the X-ray source and the breast supporting X-ray image receiver, the apparatus comprising:
a frame having a cross member,
a substantially planar compression surface having a nipple end and a chest wall end, the compression surface being pivotally attached to the frame at a pivot point between the chest wall end and the nipple end,
a lever having an opening, the lever being attached to the planar compression surface at the nipple end thereof,
a spring retaining member, having a spring retaining end, attached to the cross member of the frame and positioned through the opening in the lever, and
a spring positioned between the spring retaining end of the spring retaining member and the lever attached to the planar compression surface;

placing breast tissue on the breast supporting X-ray image receiver;

moving the compression paddle apparatus towards the breast supporting X-ray image receiver at least until contact between the chest wall end of the compression surface is made with the breast tissue and the compression paddle surface is rotated from a pre-chestwall contact resting position.

2. A method for compressing breast tissue for a mammography, the method comprising the steps of:

providing a mammography device comprising:
an imaging arm having an X-ray source end and an image receiving end,
an X-ray source attached to the imaging arm at the imaging end,
a breast supporting X-ray image receiver attached to the imaging arm at the image receiving end;

providing a rotatable compression paddle apparatus for a mammography device between the X-ray source and the breast supporting X-ray image receiver, the apparatus comprising:
a frame, including a cross member having an opening therein,
a compression surface having a chest wall end and a nipple end, pivotally attached to the frame at a pivot point located between the chest wall end and the nipple end, a lever attached to the compression surface at the nipple end thereof, a spring retaining member, having a spring retaining end, attached to the lever and positioned through the opening in the cross member of the frame, and a spring positioned between the spring retaining end of the spring retaining member and the cross member of the frame;

placing breast tissue on the breast supporting X-ray image receiver;

moving the compression paddle apparatus towards the breast supporting X-ray image receiver at least until contact between the chest wall end of the compression surface is made with the breast tissue and the compression paddle surface is rotated from a pre-chestwall contact resting position.

3. A compression paddle apparatus for a mammography device, the apparatus comprising:

a compression paddle supporting frame having a cross member;

a compression surface having a chest wall end and a nipple end, pivotally attached to the frame at a pivot point located between the chest wall end and the nipple end;

a lever attached to the compression surface at the nipple end thereof; and a spring retaining member having a spring retaining end, wherein the spring retaining member is attached to the lever and positioned through the opening in the cross member of the frame; and a spring positioned between the spring retaining end of the spring retaining member and the cross member of the frame.

4. The apparatus of claim 3, wherein the spring retaining member is hingably attached to the lever.

5. The apparatus of claim 3, wherein the spring is a coiled wire spring.

6. The apparatus of claim 3, wherein the spring is an elastomeric material.

7. The apparatus of claim 3, wherein the pivot point is located at a midpoint between the chest wall end and the nipple end of the compression surface.

8. A compression paddle apparatus for a mammography device, the apparatus comprising:

a compression paddle supporting frame having a cross member;

a compression surface having a chest wall end and a nipple end, pivotally attached to the frame at a pivot point located between the chest wall end and the nipple end;

a lever, having an opening therein, attached to the compression surface at the nipple end thereof;

a spring retaining member having a spring retaining end, wherein the spring retaining member is attached to the cross member of the frame and positioned through the opening in the lever; and a spring positioned between the spring retaining end of the spring retaining member and the lever attached to the compression surface.

9. The apparatus of claim 8, wherein the spring retaining member is hingably attached to the cross member.

10. The apparatus of claim 8, wherein the pivot point is located at a midpoint between the chest wall end and the nipple end of the compression surface.

11. The apparatus of claim 8, wherein the spring is a coiled wire spring.

12. The apparatus of claim 8, wherein the spring is an elastomeric material.

* * * * *